US008783451B2

(12) United States Patent
Slokovic et al.

(10) Patent No.: US 8,783,451 B2
(45) Date of Patent: Jul. 22, 2014

(54) UNIT DOSE BREAKABLE VIAL WITH INTEGRATED BRUSH APPLICATOR

(75) Inventors: Lorens F. Slokovic, Cleburne, TX (US); Julie L. Gremal, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/398,231

(22) Filed: Feb. 16, 2012

(65) Prior Publication Data

US 2012/0217177 A1 Aug. 30, 2012

Related U.S. Application Data

(60) Provisional application No. 61/444,308, filed on Feb. 18, 2011, provisional application No. 61/539,177, filed on Sep. 26, 2011, provisional application No. 61/568,254, filed on Dec. 8, 2011.

(51) Int. Cl.
*B65D 81/24* (2006.01)
(52) U.S. Cl.
USPC ........... 206/209; 206/15.2; 206/210; 401/132
(58) Field of Classification Search
USPC ............... 206/15.2, 15.3, 205, 209, 210, 361; 132/313, 317; 401/126–129, 132, 268, 401/269; 604/3
See application file for complete search history.

(56) References Cited

U.S. PATENT DOCUMENTS

| | | | | |
|---|---|---|---|---|
| 4,712,936 A | * | 12/1987 | Kessler | 401/129 |
| 4,889,228 A | * | 12/1989 | Gueret | 206/209 |
| 4,952,204 A | * | 8/1990 | Korteweg | 401/132 |
| 6,039,487 A | * | 3/2000 | Kristiansen | 401/126 |
| 6,315,483 B1 | * | 11/2001 | Velliquette | 401/278 |
| 6,516,947 B1 | * | 2/2003 | Van Dyke et al. | 206/361 |

(Continued)

FOREIGN PATENT DOCUMENTS

| | | |
|---|---|---|
| DE | 20213853 | 1/2003 |
| WO | 01-84977 | 11/2001 |
| WO | 02-094367 | 11/2002 |
| WO | 2012104357 A1 | 8/2012 |

OTHER PUBLICATIONS

Patent Cooperation Treaty, Notification of Transmittal of the International Search Report and the Written Opinion of the International Searching Authority, or the Declaration, Form PCT/ISA/220, Int. App. No. PCT/US2012/025558, Apr. 12, 2012.

(Continued)

*Primary Examiner* — Luan K Bui
(74) *Attorney, Agent, or Firm* — Lorenz Siddiqi

(57) ABSTRACT

A disposable sterile breakable vial includes a handle section and a vial section which are completely separable in response to a manually applied separation force. The vial section includes a sterile void dimensioned to contain a unit dose of a sterile therapeutic topical agent. An elongated member comprises a proximal portion supported by the handle section and a distal portion provided with a sterile applicator element, such as a brush. At least the applicator element is completely enclosed within the vial section with the applicator element immersed within the therapeutic topical agent. A hermetic seal between the handle and vial sections maintains sterility of at least the vial section prior to handle and vial section separation. Complete separation of the handle section and the vial section exposes the elongated member and the applicator element for topical application of the therapeutic agent saturating the applicator element.

15 Claims, 10 Drawing Sheets

(56) References Cited

U.S. PATENT DOCUMENTS

| | | |
|---|---|---|
| 6,959,808 B2 | 11/2005 | Discko |
| 7,201,577 B2 | 4/2007 | Levine |
| 7,828,142 B2 | 11/2010 | Discko |
| 8,017,655 B2 | 9/2011 | Woodward et al. |
| 8,235,617 B2* | 8/2012 | Peck et al. .............. 401/132 |
| 8,235,618 B2* | 8/2012 | Peck et al. .............. 401/132 |
| 8,337,108 B2* | 12/2012 | Bouix et al. ............. 401/133 |
| 2003/0173235 A1 | 9/2003 | Balkenhol |
| 2007/0286890 A1 | 12/2007 | Walt |
| 2009/0095316 A1 | 4/2009 | Gensch |
| 2009/0304433 A1* | 12/2009 | Peck et al. ............... 401/126 |
| 2009/0324318 A1 | 12/2009 | Wilde |
| 2010/0204335 A1 | 8/2010 | Beddingfield et al. |
| 2010/0209477 A1* | 8/2010 | Butuner et al. .......... 424/427 |
| 2012/0029470 A1* | 2/2012 | Juan et al. ............... 604/506 |
| 2012/0322882 A1 | 12/2012 | Trogden et al. |
| 2014/0037364 A1 | 2/2014 | Hartstock et al. |

OTHER PUBLICATIONS

Patent Cooperation Treaty, Notification of Transmittal of the International Search Report and the Written Opinion of the International Searching Authority, or the Declaration, Apr. 12, 2012.

* cited by examiner

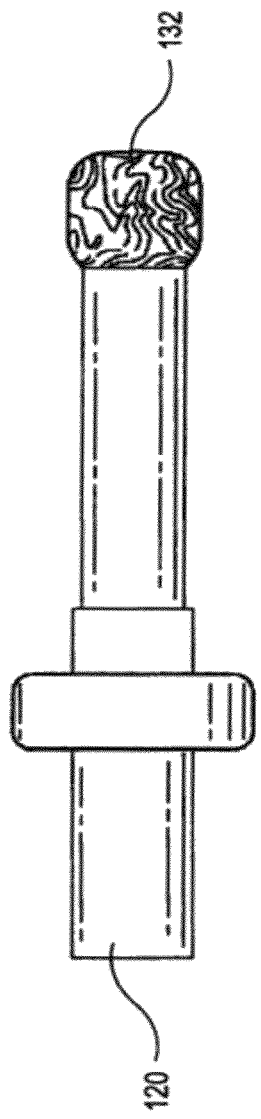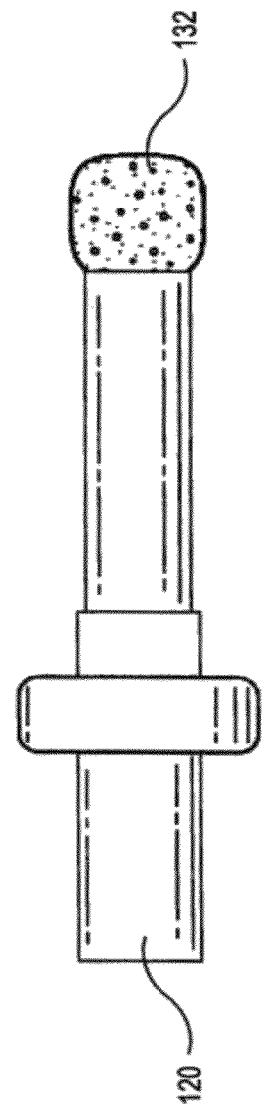
Fig. 3A
Fig. 3B

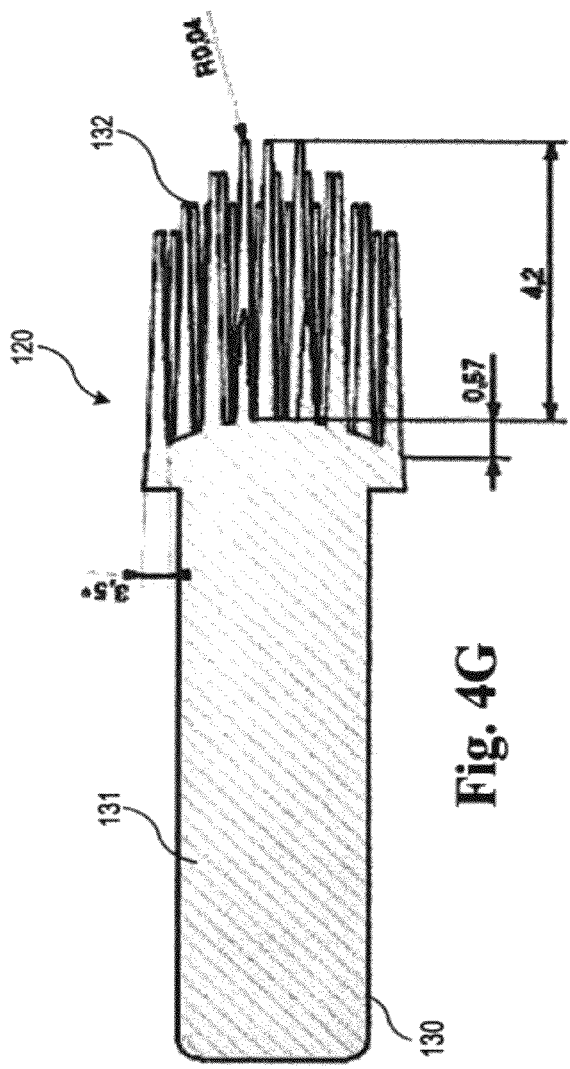
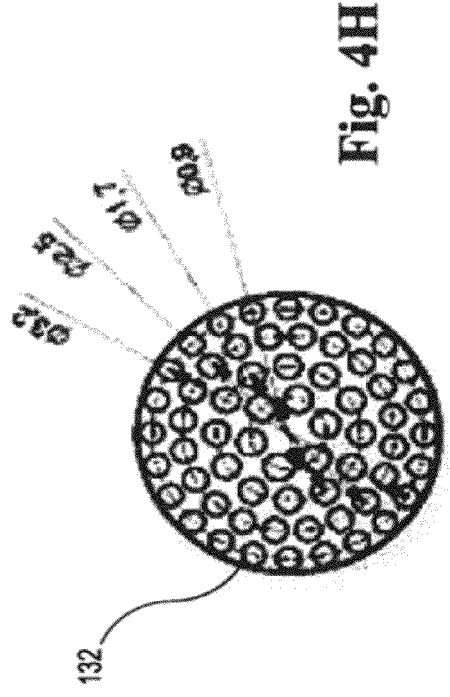
Fig. 4G
Fig. 4H

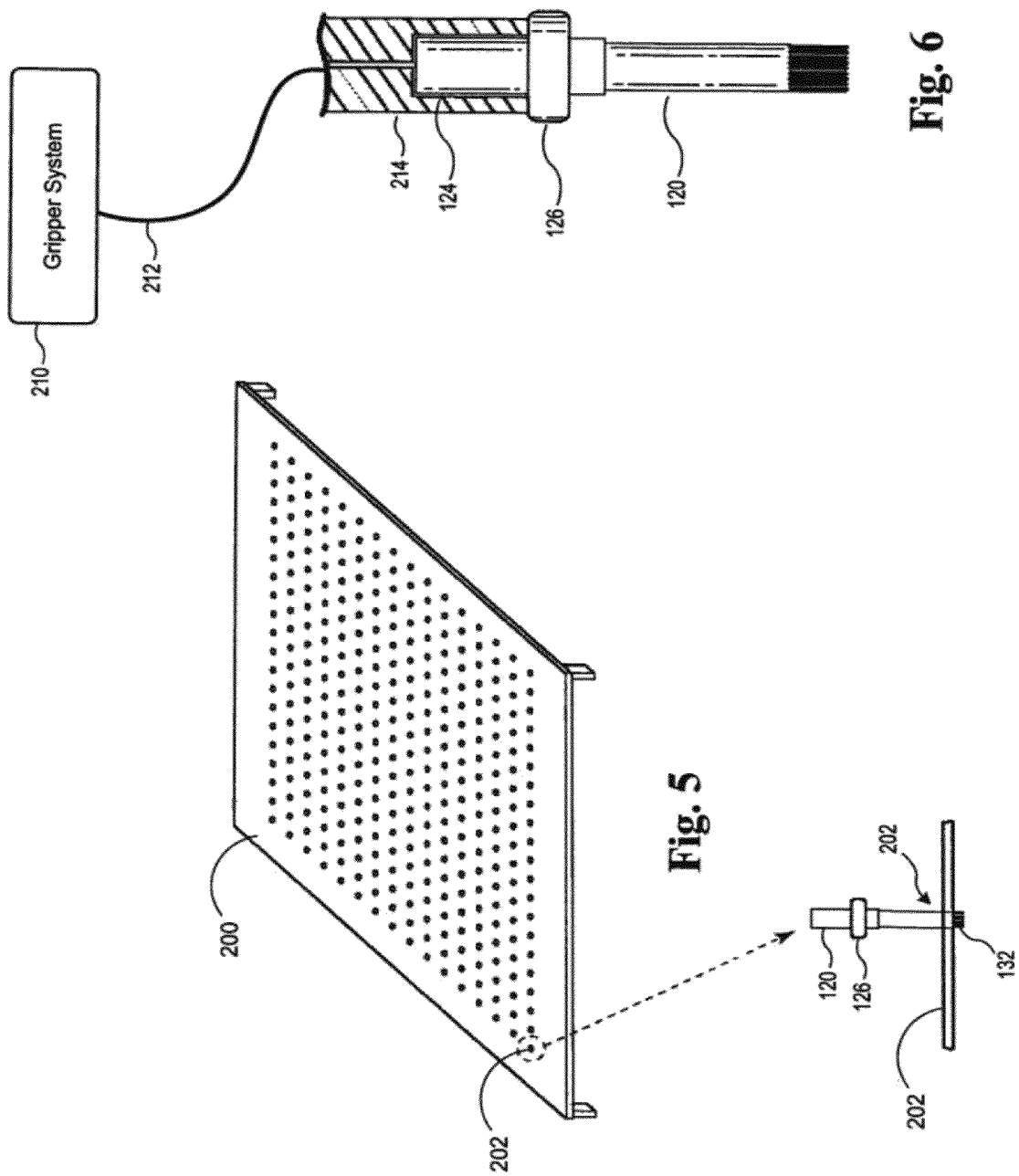

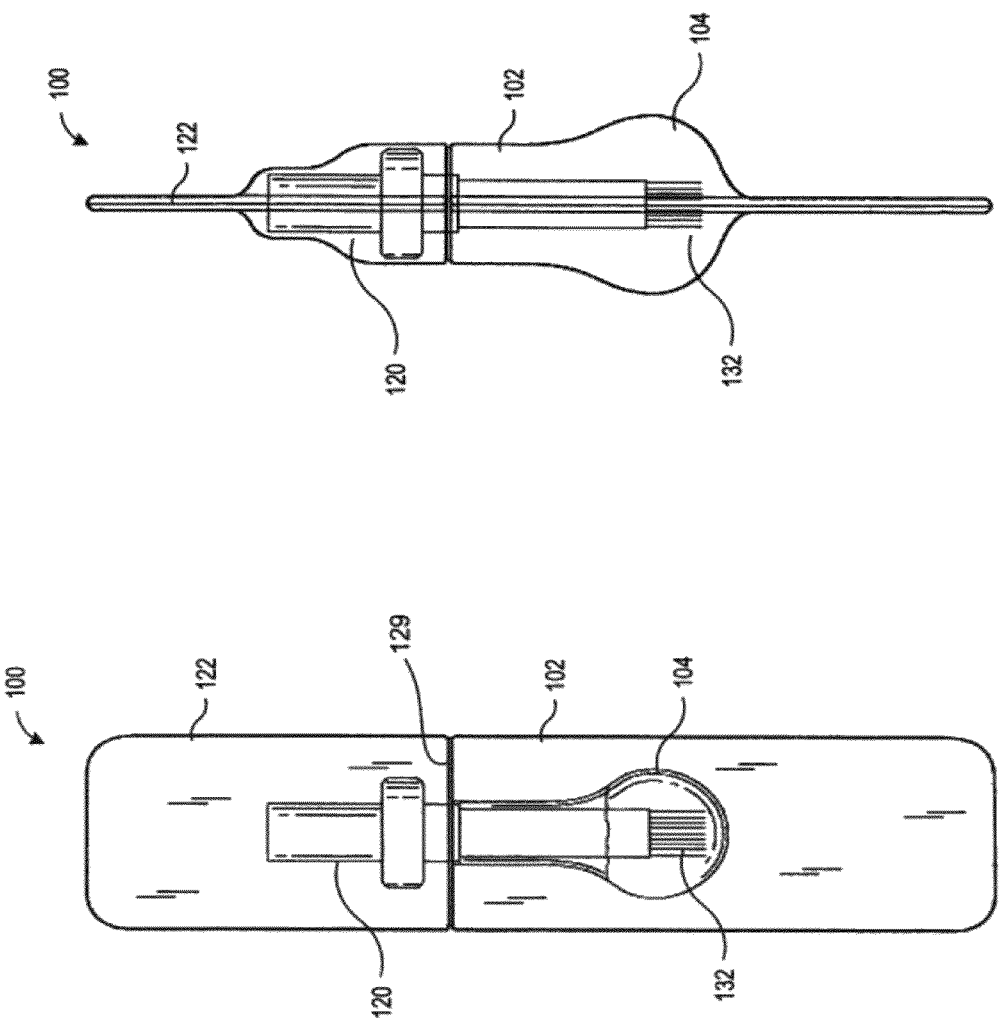

UNIT DOSE BREAKABLE VIAL WITH INTEGRATED BRUSH APPLICATOR

RELATED PATENT DOCUMENTS

This application claims the benefit of Provisional Patent Application Ser. Nos. 61/444,308, filed Feb. 18, 2011; 61/539,177 filed Sep. 26, 2011; and 61/568,254 filed Dec. 8, 2011, each of which priority is claimed pursuant to 35 U.S.C. §119(e), and incorporated herein by reference in its entirety.

SUMMARY

Embodiments of the disclosure are directed to unit dose vials with integrated applicators for topical application of a liquid contained in the vials. Embodiments of the disclosure are directed to unit dose vials with integrated applicators that maintain sterility of a liquid contained therein for topical application of the liquid to specified areas of the body. Embodiments of the disclosure are directed to a unit dose vial and applicator with an enclosed brush system for topical application of a therapeutic agent to skin at the eyelid, eyebrows, and other areas of the body.

In accordance with various embodiments, a disposable sterile apparatus for topical application of a sterile therapeutic agent includes a breakable vial comprising a handle section and a vial section. The breakable vial is completely separable into the handle section and the vial section in response to a manually applied separation force. The vial section includes a sterile void dimensioned to contain a unit dose of a sterile therapeutic topical agent. An elongated member comprises a proximal portion supported by the handle section and a distal portion provided with a sterile applicator element. At least the applicator element is completely enclosed within the vial section with the applicator element immersed within the therapeutic topical agent. A hermetic seal is provided between the handle and vial sections. The hermetic seal maintains sterility of at least the vial section prior to handle and vial section separation. Complete separation of the handle section and the vial section exposes the elongated member and the applicator element for topical application of the therapeutic agent saturating the applicator element.

According to other embodiments, a disposable, unit-dose sterile apparatus for topical application of a therapeutic agent includes a breakable vial comprising a handle section and a vial section. The breakable vial is completely separable into the handle section and the vial section in response to a manually applied separation force. The vial section includes a sterile void dimensioned to contain a unit dose of a sterile therapeutic topical agent. A sterile applicator includes a handle, a shaft, and a brush. The handle section supports the applicator handle, and the brush and at least a portion of the shaft are completely enclosed within the breakable vial with the brush extending into the sterile void and immersed in the therapeutic topical agent. A hermetic seal between the vial section and the handle section maintains sterility of the void, the therapeutic topical agent, the shaft portion, and the brush prior to handle and vial separation. Complete separation of the handle section and the vial section exposes the sterile shaft portion and the brush for topical application of the therapeutic agent saturating the brush.

In some embodiments, the breakable vial, the applicator, and the brush are formed from disparate materials. In other embodiments, at least two of the breakable vial, applicator, and brush are formed from the same material. In further embodiments, the breakable vial, applicator, and brush are formed from the same material. According to various embodiments, the therapeutic topical agent comprises a property of a tough extractable profile, and the breakable vial, applicator, and brush are formed from the same material, such as low density polyethylene.

Various sterile and therapeutic topical agents can be contained in the breakable vial, such as a prostaglandin analog, a prostamide, prostaglandin C-1 ethyl amides, bimatoprost including its prodrugs, latanoprost, travaprost, and a pharmacological agent such as a wound healing agent. In some embodiments, the therapeutic topical agent contained in the breakable vial may be in a formulation such as the commercially available hair growth product LATISSE®, which can be applied to the skin along an eyelid or eyebrow using the applicator brush integrated in the handle section of the breakable vial.

According to further embodiments, various methods involve applying a force to each of a first section and a second section of a disposable breakable vial. The first section of the breakable vial includes a vial having a sterile void dimensioned to contain a unit dose of a sterile therapeutic topical agent. The second section of the breakable vial includes a handle, an elongated sterile applicator supported by the handle, and a brush provided at a distal end of the applicator extending into the sterile void of the vial and immersed in the therapeutic topical agent. Various methods further involve facilitating complete separation of the first and second sections preferentially along a separation feature in response to the force applied to each of the first and second sections, wherein complete separation of the first and section sections breaks a hermetic seal between the vial and the handle and brush, and exposes the handle and brush for topical application of the therapeutic agent saturating the brush. Some methods involve applying a therapeutic topical hair growth agent to skin along an eyelid or eyebrow using the exposed handle and brush.

Some embodiments of the present invention include the following:

1. A disposable sterile or non-sterile apparatus for topical application of a sterile therapeutic agent, comprising:

a breakable vial comprising a handle section and a vial section, the breakable vial completely separable into the handle section and the vial section in response to a manually applied separation force;

the vial section comprising a sterile void dimensioned to contain a unit dose of a sterile therapeutic topical agent;

a sterile applicator comprising a handle, a shaft, and a brush, the handle section supporting the applicator handle, and at least a portion of the shaft and the brush completely enclosed within the breakable vial with the brush extending into the sterile void and immersed in the therapeutic topical agent; and a hermetic seal between the vial section and the handle section that maintains sterility of the void, the therapeutic topical agent, the shaft portion, and the brush prior to handle and vial separation, wherein complete separation of the handle section and the vial section exposes the sterile shaft portion and the brush for topical application of the therapeutic agent saturating the brush.

2. The apparatus according to paragraph 1, wherein the brush remains either immersed in or fully wetted with the therapeutic topical agent irrespective of an orientation of the disposable sterile apparatus.

3. The apparatus according to paragraphs 1 or 2, wherein the hermetic seal comprises a separation feature between the handle and vial sections.

4. The apparatus according to paragraphs 1, 2 or 3 comprising a web of material between the vial and handle sections comprising a frangible separation feature.

5. The apparatus according to paragraphs 1 or 3, wherein the breakable vial and the applicator are formed from disparate materials.

6. The apparatus according to paragraph 1, wherein the breakable vial and the applicator are formed from the same material.

7. The apparatus according to paragraph 1, wherein:
the therapeutic topical agent comprises a property of a tough extractable profile; and
the breakable vial and the applicator are formed from the same material.

8. The apparatus according to paragraph 7, wherein the breakable vial and the applicator each are formed from low density polyethylene.

9. The apparatus according to paragraph 1, comprising a plurality of the apparatuses connected together by frangible members to define a card of vials.

10. The apparatus according to paragraphs 1-9, wherein the therapeutic topical agent comprises a prostaglandin analog.

11. The apparatus according to paragraph 1, wherein the therapeutic topical agent comprises prostaglandin C-1 ethyl amides.

12. The apparatus according to paragraph 1, wherein the therapeutic topical agent comprises one selected from the group consisting of bimatoprost, latanopost, travaprost or mixtures thereof 13. The apparatus according to paragraphs 1 and 12, wherein the brush comprises bristles having a coating designed to rapidly and evenly release dilute prostamide solutions to a surface of the skin or eyelid margin.

14. The apparatus according to paragraph 1, wherein the brush has a generally tapered shape comprising bristles of differing length.

15. The apparatus according to paragraph 1, wherein the brush has a generally tapered shape that serves to trap the therapeutic topical agent using capillary action.

16. The apparatus according to paragraph 1, wherein the therapeutic topical agent comprises a pharmacological agent.

17. The apparatus according to paragraph 1, wherein the therapeutic topical agent comprises one selected from the group consisting of a wound healing agent, hair growth agent, hair removal agent, antifungal, anti-inflammatory, immunomodulator, anti-neoplastic agent, wound reducing agent and an antibiotic.

18. A disposable sterile apparatus for topical application of a therapeutic agent, comprising:
a breakable vial comprising a handle section and a vial section, the breakable vial completely separable into the handle section and the vial section in response to a manually applied separation force;
the vial section comprising a sterile void dimensioned to contain a unit dose of a sterile therapeutic topical agent;
an elongated member comprising a proximal portion supported by the handle section and a distal portion provided with a sterile applicator element, at least the applicator element completely enclosed within the vial section with the applicator element immersed within the therapeutic topical agent; and
a hermetic seal between the handle and vial sections, the hermetic seal maintaining sterility of at least the vial section prior to handle section and vial section separation, wherein complete separation of the handle section and the vial section exposes the elongated member and the applicator element for topical application of the therapeutic agent saturating the applicator element.

19. The apparatus according to paragraph 18, wherein the applicator element comprises a brush or a comb.

20. The apparatus according to paragraph 18, wherein the applicator element comprises a brush having a generally tapered shape comprising bristles of differing length.

21. The apparatus according to claim 18, wherein the applicator element comprises a brush having a generally tapered shape that serves to trap the therapeutic topical agent using capillary action.

22. The apparatus according to paragraphs 18-19, wherein the applicator element comprises a sponge or an absorbent pad.

23. The apparatus according to paragraphs 18, 19, 20, 21 or 22, wherein the therapeutic topical agent comprises a prostaglandin analog.

24. The apparatus according to paragraphs 18, 19, 20, 21, and 22, wherein the therapeutic topical agent comprises prostaglandin C-1 ethyl amides.

25. The apparatus according to paragraph 18, wherein the therapeutic topical agent comprises bimatoprost, latanopost, or travaprost.

26. The apparatus according to paragraph 18, wherein the therapeutic topical agent comprises a pharmacological agent.

27. The apparatus according to paragraph 18, wherein:
the therapeutic topical agent comprises a property of a tough extractable profile; and
the breakable vial and the applicator are formed from low density polyethylene.

28. A method, comprising:
applying a force to each of a first section and a second section of a disposable breakable vial, the first section of the breakable vial comprising:
a vial having a sterile void dimensioned to contain a unit dose of a sterile therapeutic topical agent; and
the second section of the breakable vial comprising:
a handle; and
an elongated sterile applicator supported by the handle, a brush provided at a distal end of the applicator extending into the sterile void of the vial and immersed in the therapeutic topical agent; and
facilitating complete separation of the first and section sections preferentially along a separation feature in response to the force applied to each of the first and second sections;
wherein completely separating the first and section sections breaks a hermetic seal between the vial and the handle and brush, and exposes the handle and brush for topical application of the therapeutic agent saturating the brush.

29. The method according to paragraph 28, further comprising applying the therapeutic topical agent comprising a hair growth agent to an eyelid or eyebrow using the exposed handle and brush.

These and other features can be understood in view of the following detailed discussion and the accompanying drawings.

BRIEF DESCRIPTION OF THE DRAWINGS

FIGS. 3A and 3B illustrate different types of applicators that may be integrated in a unit dose breakable vial in accordance with various embodiments;

FIGS. 4E-4H show details of an application brush of a unit dose breakable vial in accordance with various embodiments;

FIG. 5 illustrates a process of positioning of an applicator during manufacture of a unit dose breakable vial in accordance with various embodiments;

FIG. 6 illustrates handling of an applicator by a vacuum gripper during manufacture of a unit dose breakable vial in accordance with various embodiments;

FIGS. 7 and 8 show different views of a unit dose breakable vial in accordance with various embodiments.

DISCLOSURE

Figure 1B:
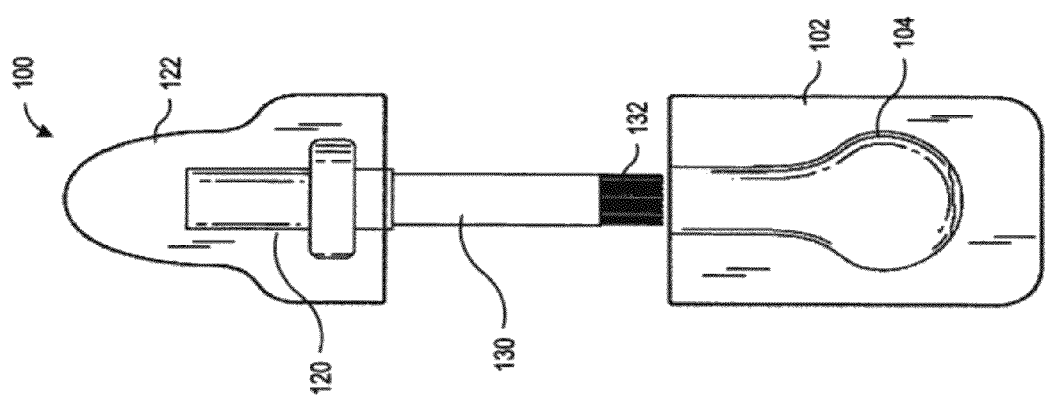
FIGS. 1A-2B show different views of a unit dose breakable vial in accordance with various embodiments.

Embodiments of the disclosure are directed to breakable unit dose vials which fully enclose a therapeutic agent and an applicator for topically applying the therapeutic agent to the skin, such as the eyelids or eyelid margin or the surface of the skin such as the scalp or skin directly under the eyebrows. The breakable vial is preferably constructed to break easily into two-pieces by a user; a handle section and a vial section. An exterior surface of the handle section is shaped for easy grasping and manipulation by the user. An interior portion of the handle section provides support for the applicator, which includes an elongated member and an applicator element, such as a brush, sponge, pad, or comb, for example, provided at the distal end of the elongated member.

Until broken into two-pieces by the user, the applicator element is immersed in the therapeutic agent contained within the vial section, with the vial section sealed to maintain sterility of the therapeutic agent and at least the applicator element. When a user breaks or opens the vial, the applicator element and handle are available. Because the applicator element is immersed in the therapeutic agent prior to separating the handle and vial sections of the breakable vial, the wetted applicator element is made available for immediate use, such as for applying the therapeutic agent on the brush to skin along the eyelids or eyebrows. Each breakable vial preferably contains a unit dose of the therapeutic agent, contains no preservative, and is disposed of after application. A unit dose is generally understood as the amount of medication administered to a patient in a single dose. The breakable vials may come in the form of a card of vials, where multiple vials are connected and individual vials may be easily detached from the card of vials. Each breakable vial of a card of vials preferably contains a single dose of the therapeutic agent for application.

The therapeutic agent may be any therapeutic to be applied topically and is generally non-preserved in unit dose form. Some therapeutic agents include agents such as bimatoprost, latanopost, travaprost or other prostaglandin analog such as prostaglandin C-1 ethyl amides, cyclosporines such as cyclosporine A; topical antiobiotics such as bacitracin, neomycin, neosporin, mupirocin and polymyxin B; and topical anti-inflammatories such corticosteroids, NSAIDS and DMARDS The therapeutic agent may be in a formulation such as a solution, emulsion or dispersion or the commercially available hair growth product LATISSE® which is a 0.03% w/v bimatoprost solution and may be non-preserved. The vials may also contain an engraving or other indicia of source or the product name, such as LATISSE®. According to some embodiments, an applicator brush is enclosed inside the breakable vial and has a handle affixed to the brush for easy handling by the user for application of one of the therapeutic agents listed above to skin along an eyelid or eyebrow. The brush typically includes a multitude of bristles which may include a particular coating designed to release dilute prostamide solutions to the surface of the skin along the eyelid or eyebrow.

Figure 1A:
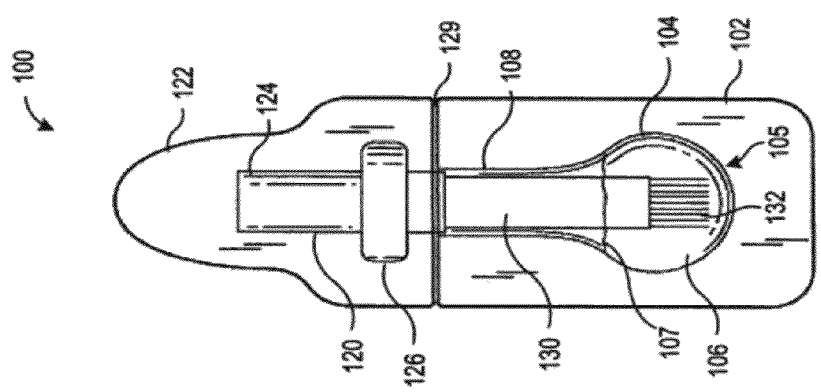
Figure 2B:
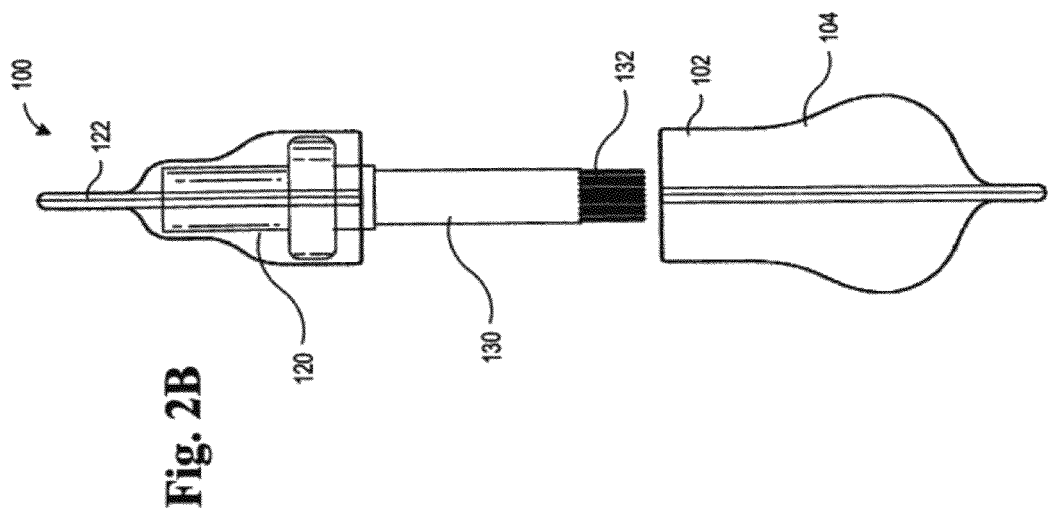
Figure 2A:
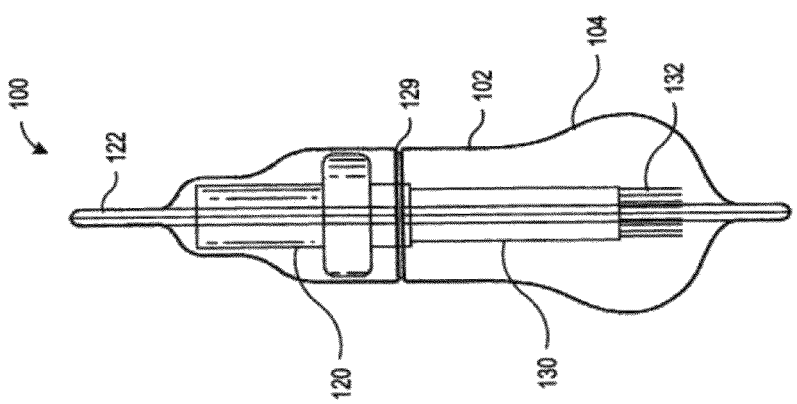

Referring to FIGS. 1A-2B, there is illustrated a unit dose breakable vial 100 in accordance with various embodiments of the disclosure. FIGS. 1A and 1B are front views of the breakable vial 100, and FIGS. 2A and 2B are side views of the breakable vial 100. FIGS. 1A and 2A show the breakable vial 100 in a sealed configuration. FIGS. 1B and 2B show the breakable vial 100 in a separated configuration. The breakable vial 100 preferably has a two-part construction which includes a vial section 102 and a handle section 122. The breakable vial 100 incorporates a separation feature 129 configured to facilitate preferential separation between the handle and vial sections 122 and 102 upon application of a manually applied force. For example, the separation feature 129 may be a frangible member or portion of the vial 100 configured to provide for preferential separation between the handle and vial sections 122 and 102 in response to a twisting force applied by a user.

The handle section 122 of the breakable vial 100 supports or otherwise incorporates a handle 124 of an applicator 120. The applicator handle 124 may include a shoulder 126 which, in some embodiments, enhances handling of the handle section 122 during manufacturing. Accordingly, the shoulder 126 may be included or excluded depending on the manner in which the breakable vial 100 is manufactured. The applicator 120 further includes a shaft 130, and an applicator element 132 is provided at a distal end of the shaft 130. The applicator element 132 is typically constructed as a separate component and incorporated at the distal end of the shaft 130 during manufacturing of the breakable vial 100.

In the embodiment shown in FIGS. 1A-2B, the applicator element 132 includes a brush. In other embodiments, the applicator element 132 may include a sponge, as is shown in FIG. 3A. In further embodiments, the applicator element 132 may include a porous or absorptive element, such as that shown in FIG. 3B. Other applicators 120 and applicator elements 132 are contemplated, such as applicators with angled shafts and applicator elements configured as combs having straight or curved profiles, for example.

According to some embodiments, the material used to fabricate the applicator 120 and applicator element 132 is different than that used to fabricate the vial 104. Suitable materials include polyethylene or polypropylene, for example. In other embodiments, the material used to fabricate the applicator 120 and applicator element 132 is the same as that used to fabricate the vial 104. Use of the same material in such embodiments is particularly advantageous when the therapeutic agent 106 contained within the vial 104 has a tough extractable profile. Solutions having a tough extractable profile have the property of attracting nearby material and debris, which can be trapped within the solution and then transferred into the vial 104. Using disparate materials for the applicator 120, applicator element 132, and vial 104 exacerbates this undesirable property, whereas use the same or similar materials for these component reduces or eliminates the adverse impact of this property. In one embodiment, the applicator 120, applicator element 132, and vial 104 are fabricated from low density polyethylene (LDPE), respectively.

The vial section 102 incorporates a vial 104 defining a void dimensioned to contain a prescribed volume of a liquid 106. The vial 104 illustrated in FIGS. 1A-2B is shown to have a bulbous distal section 105 and a proximal tapered section that transitions into a proximal neck 108. In other embodiments, the vile 104 can have a different shape, such as a generally elliptical shape with little or no proximal neck 108 or a more columnar shape, for example. The diameter of the neck 108 is preferably large enough to accommodate the diameter or width of the applicator shaft 130, preferably leaving a small gap therebetween. The volume and shape of the vial 104 are preferably selected so that the applicator element 132 remains immersed in the liquid 106 or otherwise remains wet when the breakable vial 100 is in its sealed configuration, irrespective of the orientation of the breakable vial 100.

As is shown in FIG. 1A, the vial 104 is filled with liquid 106 or another composition such as a gel to a fill line 107 shown approximately between the bulbous distal section 105 and proximal neck 108. In some embodiments, the vial 104 is filled with liquid 106 such that the applicator element 132 remains fully immersed in the liquid 106 irrespective of the orientation of the breakable vial 100. In other embodiments, the liquid 106 within the vial 104 is sufficient in volume to maintain the applicator element 132 in a continuous wet state, irrespective of the orientation of the breakable vial 100 and notwithstanding that the applicator element 132 may not be completely immersed in the liquid 106 at all times. The requirement for either complete or partial continuous immersion of the applicator element 132 in the liquid 106 typically depends on the composition of one or both of the liquid 106 and the applicator element 132. It is noted that the volume defined by the gap between the outer surface of the applicator shaft 130 in the inner surface of the neck 108 should be accounted for when determining the necessity for complete or partial applicator element immersion within the liquid 106.

The volume of the liquid 106 contained within the vial 104 preferably defines a unit dose of a therapeutic topical agent, and the breakable vial 100 is preferably manufactured to be a disposable article. The volume of liquid 106 defining a unit dose typically varies in accordance with the type of therapeutic topical agent contained within the vial 104. Examples of useful therapeutic topical agents dispersed within the liquid 106 that can be contained within the breakable vial 100 include a prostaglandin analog such as a prostamide, prostaglandin C-1 ethyl amides, bimatoprost, latanopost, or travaprost, and a variety of pharmacological agents, such as a wound healing agent or topical antibiotic, anti-inflammatory or antifungal. The volume of the liquid 106 contained within the vial 104 typically ranges from about 0.03 mL to about 0.8 mL. In some embodiments, the vial 104 can be dimensioned to contain a very small volume of the liquid 106, such as about 0.01 mL or 0.02 mL, for example.

According to some embodiments, the separation feature 129 provided between the handle and vial sections 122 and 102 comprises a sealing material, such as a resin, which forms a liquid-tight seal between the handle and vial sections 122 and 102. In other embodiments, the separation feature 129 can define a thinned circumferential section of material (e.g., a thin web of polymeric material) that is used to form the handle and vial sections 122 and 102 during manufacturing, such as by a molding technique. In some embodiments, the liquid-tight seal provided by the separation feature 129 defines an airtight seal, such as a hermetic seal. The need for a liquid-tight seal or a hermetic seal depends largely on the composition of the fluid 107 contained within the vial 104 and the need (or lack thereof) for sterility.

In accordance with various embodiments, the breakable vial 100 is constructed as a disposable sterile article configured to facilitate topical application of a therapeutic agent to a specified portion of a user's body such as the surface of the skin, eyelid, eyelid margin, mucous membrane, surface of the eye, finger nails and toe nails, wound repair and scar reduction. According to such embodiments, the disposable sterile article includes a breakable vial 100 comprising a sterile void or vial 104 dimensioned to contain a unit dose of a sterile therapeutic topical agent. A sterile applicator 120 is completely enclosed within the breakable vial 100 and preferably includes a handle section 120 that supports a brush section 132, for example. At least the brush section 132 of the sterile applicator 120 extends into the sterile void of the vial 104 and is immersed in the therapeutic topical agent. A hermetic seal 129 is provided between the vial 104 and the handle section 122 which maintains sterility of the void, the therapeutic topical agent, and the portion of the applicator 120 extending into the vial 104. The breakable vial 100 is capable of complete separation into first and second sections in response to a manually applied force which exposes the sterile applicator 120 for topical application of the therapeutic agent 106.

According to some embodiments, the therapeutic agent is one that promotes eyelash growth (e.g., LATISSE®), the volume of the vial 104 is sufficient to contain a unit dose of the agent without a preservative, and the applicator 120 includes an integrated brush applicator 132 configured to transfer the unit dose of the agent from the vial 104 to the user's skin along the eyelash. According to other embodiments, the therapeutic agent is one that promotes wound healing, and the volume of the vial 104 is sufficient to contain a unit dose of the wound healing agent. In the context of wound healing agents, a unit dose may be defined as a dose sufficient to cover and "average" size wound, for example. It is noted that the volume of a particular therapeutic agent constituting a "unit dose" will typically differ in accordance with the particular agent's composition and effectiveness, and the body surface to be treated. It is further noted that the volume of a particular therapeutic agent constituting a "unit dose" can differ based on the amount of coverage defining the region of treatment.

Figure 4B:
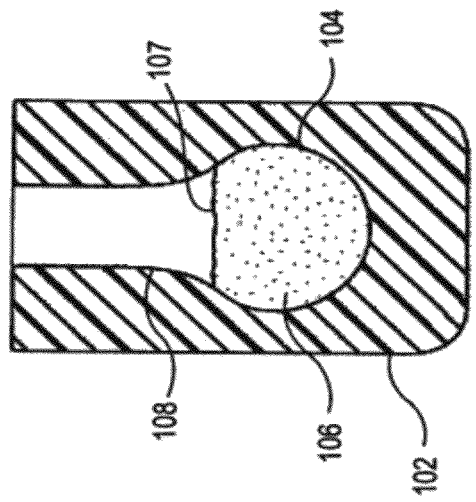
FIGS. 4A-4D show components of a unit dose breakable vial at different stages of manufacture in accordance with various embodiments.
Figure 4A:
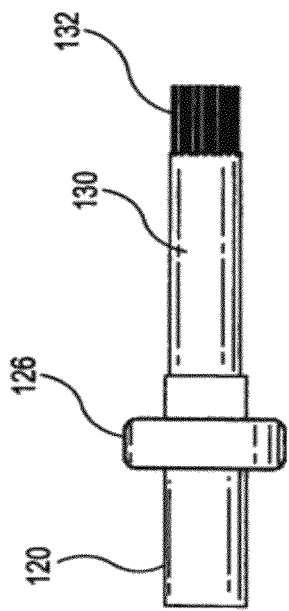
Figure 4D:
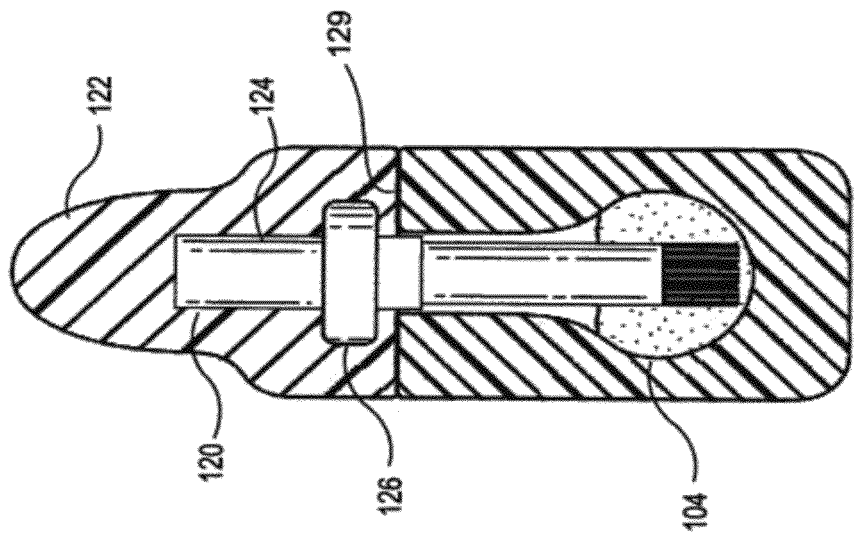
Figure 4C:
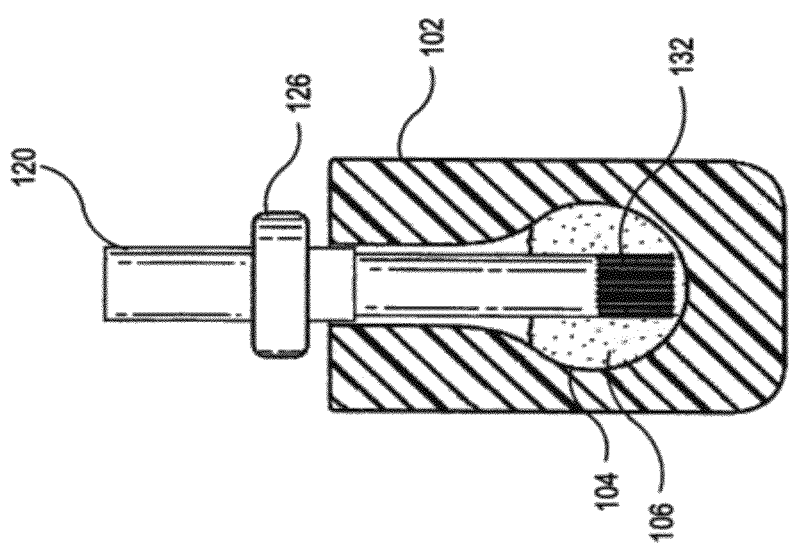
Figure 4E:
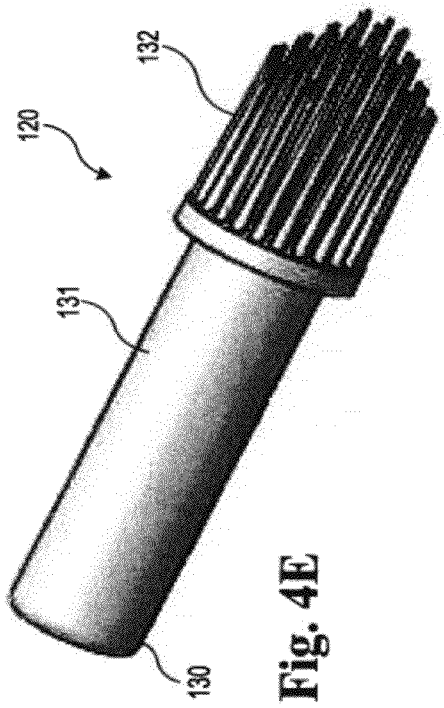
Figure 4F:
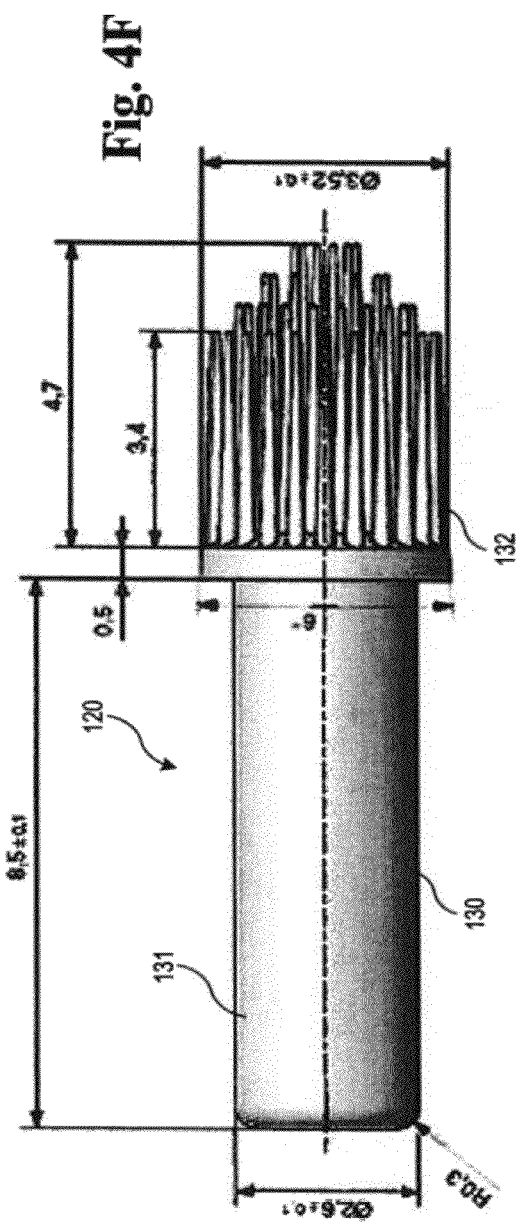

A process for fabricating a unit dose breakable vial 100 having an integrated brush applicator in accordance with various embodiments is illustrated in FIGS. 4A-4D. FIG. 4A shows an applicator 120 having a brush applicator 132 disposed at a proximal end of the applicator's shaft 130. In this illustrative embodiment, the applicator 120 is pre-fabricated prior to being integrated into a unitary breakable vial article. FIG. 4B shows the vial section 102 which includes a distal vial 104 having a bulbous shape and a proximal neck 108. In FIG. 4B, a liquid 106 comprising a therapeutic agent fills the vial 104 to a predetermined fill line 107. FIG. 4C shows the applicator 120 inserted within the vial section 102, such that the brush applicator 132 is fully immersed within the liquid 106. With the brush applicator 132 positioned within the vial section 102, the handle section 122 is formed so as to encapsulate the exposed proximal portion of the applicator 120 including the handle 124 and shoulder 126, as shown in FIG. 4D. Forming the handle section 122 in this manner creates the separation feature 129 which, according to this embodiment, also serves as a hermetic seal that maintains sterility of the applicator 120, brush applicator 132, vial 104, and liquid 106.

According to some embodiments, and with reference to FIGS. 4E-4H, the applicator 120 includes two primary components; a polypropylene adaptor 131, which defines part of the applicator's shaft 130, and a low density polyethylene brush applicator 132. The adaptor 131 defines a structural interface between the unit dose vial 104 and the applicator brush 132 in order to create an integral brush handle 124 after the vial 104 has been opened.

The applicator brush 132 is preferably a soft injected molded brush, configured to apply a fine line of solution (e.g., LATISSE®) on the upper eyelid margin with no run off of the solution. In the embodiment illustrated in FIGS. 4E-4H, the applicator brush 132 includes 62 filaments having a length ranging between about 3.4-4.7 mm and preferably formed out of sterilizable low density polyethylene. The applicator brush 132 utilizes a tapered design to trap the solution using capillary action, and is configured to dispense the solution upon application to the upper lid margin once the surface tension of the solution is broken during the eyelid application phase.

According to some embodiments, the unit dose breakable vial 100 is fabricated using a sterile blow-fill-seal (BFS) manufacturing technique. A BFS manufacturing process typically involves aseptic fabrication of a vessel which is formed, filled, and sealed in a continuous automated process within a sterile enclosed region within the fabrication machinery. Reference is made to FIGS. 5 and 6, together with FIGS. 4A-4H, in the following representative fabrication method. FIG. 5 shows a pre-fabricated applicator 120 positioned above a hole 202 provided in a holder plate 200. The applicator 120 is advanced through the hole 202 until the shoulder 126 of the applicator 120 contacts the holder plate 200. This process is repeated for seating a multiplicity of applicators 120 within holes 202 of the holder plate 200. With the holder plate 200 populated with applicators 120, a gripper system 210, depicted in FIG. 6, is used to place each applicator 120 into the vial section 102 of a unit dose breakable vial 100 (as is shown in FIG. 4C) at the appropriate time in the manufacturing process.

In a separate process, the vial section 102 is formed using a pharmaceutical-grade plastic resin (e.g., polyethylene or polypropylene) typically using a vertical heat extrusion process. The extruded vial section 102 is placed within a two-part mold, and an extraneous top portion of the vial section 102 is cut and removed. A needle mandrel is moved into position relative to the mold and used to inflate the plastic resin to form the void defining the neck 108 and vial 104 of the vial section 102. A filling mandrel is then moved into position relative to the opening of the neck 108 of the vial section 102. A predetermined volume of liquid 106, such as a liquid comprising a therapeutic topical agent, is transferred into the vial 104.

After completion of the liquid filling process, a gripper system 210, depicted in FIG. 6, is used to transfer the applicator 120 from the holder plate 200 into the vial section 102. The gripper system 210 includes a vacuum gripper 214 and a tube 212 fluidly coupled to a vacuum source. The vacuum gripper 214 is configured to fit over the applicator handle 124 and matingly contact the shoulder 126 of the applicator 120. The gripper system 210 pulls a vacuum sufficient to form a vacuum seal between the vacuum gripper 214 and the shoulder 126 of the applicator 120, allowing the gripper system 210 to move the applicator 120 in accordance with a predefined sequence of movements. With the applicator 120 properly positioned within the vial section 102, a top mold is moved into mating engagement with the mold supporting the vial section 102. Plastic resin is flowed into the mold to form the handle section 122 and the hermetic seal including the separation feature 129. Upon completion of the molding process, the breakable vial 100 is transferred from the sterile environment of the fabrication machinery to a non-sterile work area where additional processing occurs, such as labeling and packaging.

Figure 9:
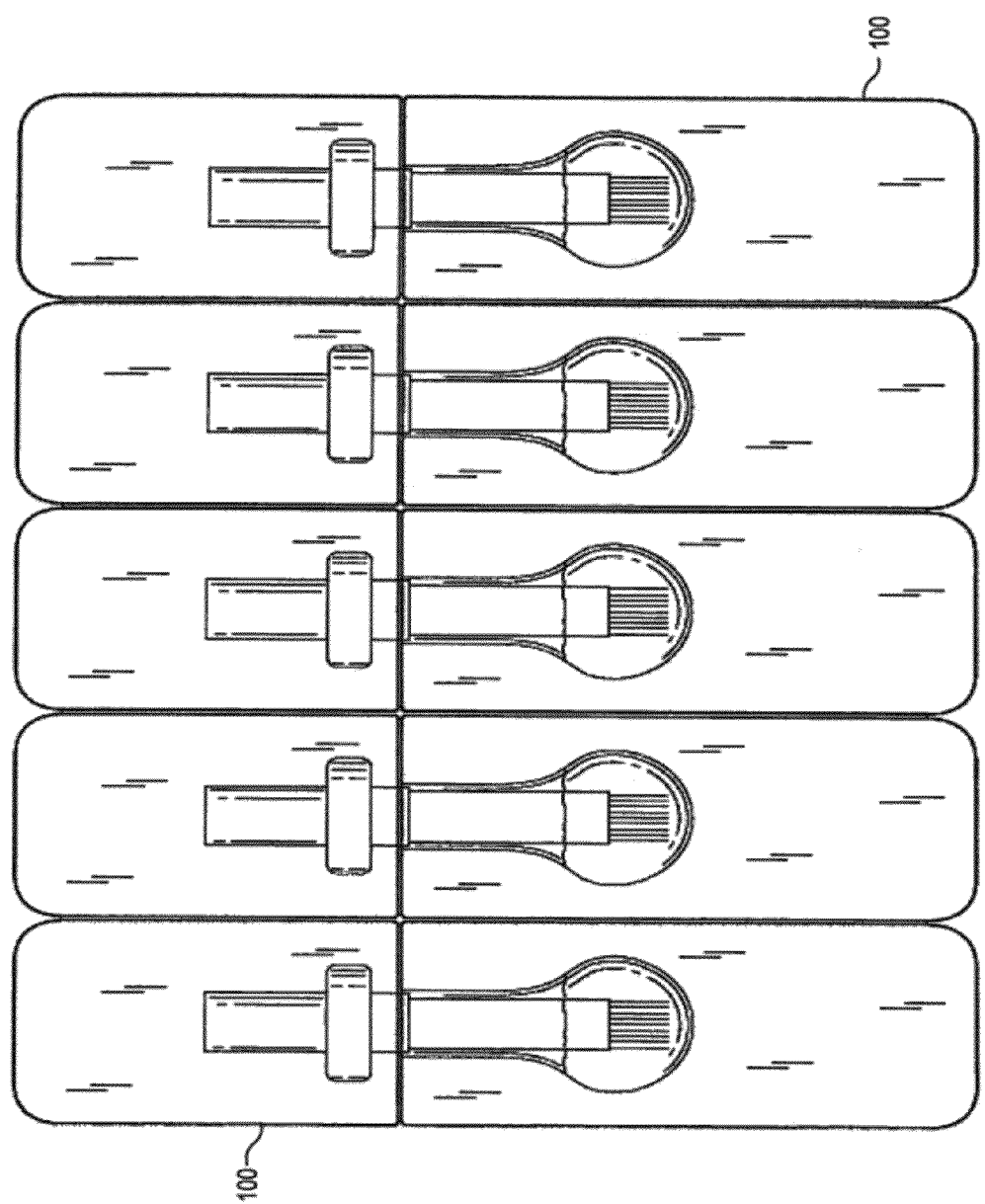
FIG. 9 illustrates a card of unit dose breakable vials of the type shown in FIGS. 7 and 8 in accordance with various embodiments.

FIGS. 7-9 illustrate a breakable vial 100 which is suitable for mass production using a BSF manufacturing process in accordance with embodiments of the disclosure. The breakable vial 100 shown in FIGS. 7 and 8 is similar to that shown in prior Figures, except for the generally rectangular shape of the handle section 122. FIG. 9 shows several unit dose breakable vials 100 connected and arranged to form a card of vials. Individual breakable vials 100 of the card of vials are preferably connected together using a frangible member or thinned portion of the card of vials that facilitates easy separation of individual breakable vials 100 from the card of vials. For example, the frangible members may be formed as a thinned portion of the plastic material used to form the vials 100 during the BFS molding process.

It is understood that the shape, size, and dimensions of the handle and vial sections 122 and 102 of the breakable vial 100 can differ from the embodiments illustrated in the Figures. For example, the breakable vial 100 can incorporate curved portions, surface features, and indicia or engravings (e.g., "LATISSE®") that provide for enhanced aesthetics, ergonomics, and product identification.

The various embodiments disclosed herein are generally described in the context of unit dose breakable vials containing sterile fluidic therapeutic agents. It is understood, however, that embodiments of the disclosure have applicability in other contexts, such as for containing fluids other than those comprising therapeutic agents or fluids not requiring sterility. Accordingly, it is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A disposable sterile or non-sterile apparatus containing a sterile therapeutic agent, comprising:
    a breakable vial comprising a handle section and a vial section, the breakable vial completely separable into the handle section and the vial section in response to a manually applied separation force;
    the vial section comprising a sterile void containing a unit dose of the sterile therapeutic topical agent, wherein the therapeutic topical agent comprises a prostaglandin analog;
    a sterile applicator comprising a handle, a shaft, and a brush, the handle section supporting the handle, and at least a portion of the shaft and the brush completely enclosed within the breakable vial with the brush extending into the sterile void and immersed in the therapeutic topical agent, wherein the brush has a generally tapered shape comprising bristles of differing length that serves to trap the therapeutic topical agent using capillary action and comprises multiple bristles molded thereto; and
    a hermetic seal between the vial section and the handle section that maintains sterility of the void, the therapeutic topical agent, the shaft, and the brush prior to separation of the handle section and vial section, wherein complete separation of the handle section and the vial section exposes the sterile shaft and the brush for topical application of the therapeutic agent saturating the brush.

2. The apparatus according to claim 1, wherein the brush remains either immersed in or fully wetted with the therapeutic topical agent irrespective of an orientation of the disposable sterile apparatus.

3. The apparatus according to claim 1, wherein the hermetic seal comprises a separation feature between the handle and vial sections.

4. The apparatus according to claim 1, comprising a web of material between the vial and handle sections comprising a frangible separation feature.

5. The apparatus according to claim 1, wherein the breakable vial and the applicator are formed from disparate materials.

6. The apparatus according to claim 1, wherein the breakable vial and the applicator are formed from the same material.

7. The apparatus according to claim 1, wherein:
the prostaglandin analog comprises a property of a tough extractable profile; and
the breakable vial and the applicator are formed from the same material.

8. The apparatus according to claim 7, wherein the breakable vial and the applicator each are formed from low density polyethylene.

9. The apparatus according to claim 1, comprising a plurality of the apparatuses connected together by frangible members to define a card of vials.

10. The apparatus according to claim 1, wherein the prostaglandin analog comprises prostaglandin C-1 ethyl amides.

11. The apparatus according to claim 1, wherein the prostaglandin analog is selected from the group consisting of bimatoprost, latanoprost, travaprost and mixtures thereof.

12. The apparatus according to claim 1, wherein the bristles are coated with a coating designed to rapidly and evenly release prostaglandin analog to a surface of the skin or eyelid margin.

13. A disposable sterile apparatus containing a therapeutic topical agent, comprising:
a breakable vial comprising a handle section and a vial section, the breakable vial completely separable into the handle section and the vial section in response to a manually applied separation force;
the vial section comprising a sterile void containing a unit dose of the sterile therapeutic topical agent, wherein the therapeutic topical agent comprises a prostaglandin analog;
an elongated member comprising a proximal portion supported by the handle section and a distal portion provided with a sterile applicator element, at least the applicator element completely enclosed within the vial section with the applicator element immersed within the therapeutic topical agent, wherein the applicator element comprises a brush with a generally tapered shape comprising bristles of differing length that serves to trap the therapeutic topical agent using capillary action and with multiple bristles molded thereto; and
a hermetic seal between the handle section and vial section, the hermetic seal maintaining sterility of at least the vial section prior to handle section and vial section separation, wherein complete separation of the handle section and the vial section exposes the elongated member and the applicator element for topical application of the therapeutic agent saturating the applicator element.

14. The apparatus according to claim 13, wherein the prostaglandin analog comprises prostaglandin C-1 ethyl amides.

15. The apparatus according to claim 13, wherein the prostaglandin analog comprises bimatoprost, latanoprost, or travoprost.

* * * * *